United States Patent [19]

Katsoulis et al.

[11] Patent Number: 5,548,052
[45] Date of Patent: Aug. 20, 1996

[54] SILANE MODIFIED POLYOXOMETALATE ANIONS

[75] Inventors: Dimitris E. Katsoulis, Midland; John R. Keryk, Rhodes, both of Mich.

[73] Assignee: Dow Corning Corporation, Midland, Mich.

[21] Appl. No.: 364,336

[22] Filed: Dec. 27, 1994

[51] Int. Cl.$^6$ .................. C08G 77/22; C08G 77/398
[52] U.S. Cl. ................. 528/10; 528/395; 528/32; 528/38; 528/40; 556/10; 556/57; 556/63
[58] Field of Search .................. 528/395, 32, 10, 528/38, 40; 556/10, 57, 63

[56] References Cited

U.S. PATENT DOCUMENTS 5,391,638  2/1995  Katsoulis et al. .................. 525/389

OTHER PUBLICATIONS

Knoth; J. Am. Chem. Society, 1979, 101:3, 759–760.
Judeinstein, P. et al.; J. Chem. Soc., Dalton Trans., 1991, 1991–1997.
Judeinstein, P.; Chem. Mater. (1992) 4, 4–7.
Ammari, N. et al,; New J. Chem., (1991) 15, 607–608.
Pope, M.; "Heteropoly and Isopoly Oxometalates", 1983, pp. 1–32.
Pope, M. et al.; Agnew. Chem., (International English Ed.) 30 (1991) pp. 34–48.

Tsigdinos, G.; "Heteropoly Compounds of Molybdenum & Tungsten". pp. 1–64.
Keggin, J. F.; Nature, 131 (1933) 908–909.
Knoth; J. Am. Chem., Soc., 1979, 101:3, 759–760.
Judeinstein, P. et al.; J. Chem. Soc., Dalton Trans., 1991, 1991–1997.
Judeinstein, P.; Chem. Mater. (1992) 4, 4–7.
Ammari, N. et al., New J. Chem. (1991) 15, 607–608.

Primary Examiner—Margaret W. Glass
Attorney, Agent, or Firm—Patricia M. Scaduto

[57] ABSTRACT

Silane modified polyoxometalate anions represented by the formula $YZ(SiRR')_n$ were prepared by reacting a silane having two hydrolyzable groups with a lacunary polyoxometalate anion. In the formula $YZ(SiRR')_n$, Z is $M_{11}O_{39}^{-12}$, $M_9O_{34}^{-14}$ or $M_{17}O_{61}^{-20}$, where M is tungsten or molybdenum; Y is $As^{+5}$, $Si^{+4}$, $B^{+3}$, $Ge^{+4}$, $P^{+5}$ or $Fe^{+5}$ when Z is $M_{11}O_{39}^{-12}$, Y is $Si^{+4}$, $Ge^{+4}$, or $P^{+5}$ when Z is $M_9O_{34}^{-14}$ and Y is $As_2^{+10}$ or $P_2^{+10}$ when Z is $M_{17}O_{61}^{-20}$; R is selected from the group consisting of monovalent hydrocarbon radicals having from 1 to 24 carbon atoms, monovalent halogenated hydrocarbon or carbon radicals having from 1 to 24 carbon atoms and monovalent hydrocarbon radicals having from 1 to 24 carbon atoms substituted with an epoxy group, an amino group, a mercapto group or a methacrylo group; R' is a hydrogen atom or R and n represents the number of $(=SiRR')^{+2}$ groups bonding to the polyoxometalate anion and has a value from 1 to 3.

10 Claims, No Drawings

SILANE MODIFIED POLYOXOMETALATE ANIONS

BACKGROUND OF THE INVENTION

1. Field of the Invention

This invention relates to the modification of inorganic metal oxide anions, referred to as polyoxometalate anions, by the reaction with silanes having two hydrolyzable groups.

2. Background Information

Although the vast majority of metal oxides are insoluble or have a limited solution chemistry, as the chemical literature points out there is an important exception. This exception includes a class of oxides that are soluble in aqueous or nonaqueous solutions, charged and derived from polyvalent metals such as molybdenum, tungsten and less frequently vanadium, niobium or tantalum, or mixtures thereof, in their highest oxidation states. These oxides are referred to in the literature as "isopolyanions" when only a polyvalent metal and oxygen are involved and can be represented by the formula $(M_mO_y)^{p-}$. If an additional metallic or non-metallic element is present these oxides are referred to as "heteropolyanions" and can be represented by the formula $(X_xM_mO_y)^{q-}$. Polyoxometalate anions fall into the latter category.

In the formulae described above, M is a polyvalent metal of the type already described, X is the "heteroatom" and can be almost any element in the periodic table, other than a noble gas, O is oxygen, x, m, and y are integers where x<<m, and p and q represent the charge on the anion. This charge on the anion can be calculated by multiplying the valences of X, M and O by the value of the integer x, m and y associated with that atom and adding the products together.

Although a majority of polyoxometalate anions have been formed in aqueous solution, nonaqueous syntheses have also been developed. A thorough discussion of polyoxometalate anions can be found in a text by Michael Thor Pope entitled "Heteropoly and Isopoly Oxometalates" published in 1983 by Springer-Verlag. As discussed therein, these anions may generally be isolated from solution by addition of cations, typically alkali metals, $NH_4^+$ or $R_4N^+$, where R represents a monovalent hydrocarbon. The type of cation will affect the chemical and physical properties of the polyoxometalate anion, including its solubility, and the properties of reaction products of the polyoxometalate anion.

The chemical literature also points out that the structures of polyoxometalate anions seem to be controlled by the electrostatic and radius-ratio principles seen for extended ionic lattices. Although there are a very large number of known polyoxometalate anions, investigators have found that most of these can be characterized by relatively few structures. These structures consist of groups of $MO_6$ octahedra surrounding $XO_4$ tetrahedra that share edges, corners and occasionally faces with adjacent polyhedra.

The structure of a number of polyoxometalate anions is discussed in the above referenced article by Pope, in a text by M. Pope and A. Muller in Angew. Chem., (International English Edition), 30 (1991) 34–48 and in an article entitled "Heteropoly Compounds of Molybdenum and Tungsten" by G. Tsigdinos that is part of a collection entitled Topics in Current Chemistry, 76 (1978) 1–64.

The structure of a particular polyoxometalate anion, the heteropolyacid $H_3PW_{12}O_{40} \cdot 6H_2O$, is described by J. F. Keggin, in Nature, 131 (1933) 908–909. The acidic anion was determined to be a coordinated structure having a central $PO_4$ tetrahedron group surrounded by 12 $WO_6$ octahedra groups, linked together by shared oxygen atoms. Polyoxometalate anions having the polyhedron type structure are known as having a Keggin structure.

Keggin structure anions of the formula $(XM_{12}O_{40})^{n-}$ where M is molybdenum or tungsten and X is $As^{+5}$, $Si^{+4}$, $B^{+3}$, $Ge^{+4}$, $P^{+5}$, $Fe^{+3}$ or $Co^{+2}$ have been reported in the literature. When X is silicon and M is tungsten or molybdenum, n is 4. Under mildly basic conditions, one or more of the MO groups from a polyoxometalate anion may be removed to form a deficient or "lacunary" structure. The structure resulting from removal of one MO group can be represented by the formula $(XM_{11}O_{39})^{n-}$. In the example given above when X is silicon and M is tungsten or molybdenum, n is 8. The vacancy left by the departing group can be filled with other atoms or groups.

Another common structure of polyoxometalate anions is referred to as a Dawson structure and is represented by the formula $(X_2M_{18}O_{62})^{n-}$. The heteroatom represented by X in this structure is $P^{5+}$ or $As^{5+}$. A "lacunary" Dawson structure can also be formed by the removal of one or more MO groups. When one MO group is removed (which is the most common case) the "lacunary" Dawson structure is represented by the formula $(X_2M_{17}O_{61})^{n-}$.

Reactions of the lacunary polyoxometalate anion $W_{11}SiO_{39}^{8-}$ with $RSiCl_3$ where R is $C_2H_5$, $C_6H_5$, $NC(CH_2)_3$ or $C_3H_5$ in an unbuffered aqueous solution have been reported by Knoth, J. Am. Chem. Soc., 1979, 101:3, 759–760. Knoth determined that the $WO^{4+}$ unit required for a complete or "non-lacunary" structure was replaced with $(RSi)_2O^{4+}$ so the anion product corresponded to the composition $(RSi)_2W_{11}SiO_{40}^{4-}$. The structure Knoth postulated for this product, which was later confirmed, required that an oxygen atom bridge the two silicon groups that had been added to the polyoxometalate anion reactant.

P. Judenstein, et al., J. Chem. Soc., Dalton Trans., (1991) 1991–1997, reported the synthesis in water and acetonitrile of polyoxometalate salts or acids having the general formula $[R]_4[SiW_{11}O_{40}(SiR'')_2]$ where R=$H^+$, $K^+$, or $NR'_4^+$, R'=methyl or butyl and R''=ethyl, vinyl, phenyl or decyl. The experiments described the reaction of $W_{11}SiO_{39}^{8-}$ with various R''$SiX_3$ where X represented chlorine or ethoxy and R'' was as described above. The resulting structure of the reaction products was determined to be as described by Knoth such that an oxygen atom bridged the two silicon groups that were added.

Judenstein, Chem. Mater. (1992) 4, 4–7, describes the synthesis of negatively charged macromolecules by incorporating organically functionalized polyoxometalate anions in an organic polymeric backbone. The organically modified polyoxometalate anion was obtained by reacting $W_{11}SiO_{39}^{8-}$ with $RSiCl_3$ where R was vinyl, allyl or methacryl, or $RSi(OEt)_3$ where R was styryl and the reaction products obtained therefrom were then reacted further using a free radical polymerization.

Ammari, et al. New. J. Chem. (1991) 15, 607–608, describes the reaction of the trivacant $W_9SiO_{34}^{10-}$ with $RSiCl_3$ where R was alkyl or aryl in dry acetonitrile.

Copending U.S. application Ser. No. 08/172,787 now U.S. Pat. No. 5,391,638, provides organosiloxane compounds containing silicon-bonded polyoxometalate structures that are present as pendant groups and methods for their preparation. These methods include reacting a polysiloxane containing two or three hydrolyzable groups on the terminal silicon with a lacunary polyoxometalate anion and reacting a polyorganosiloxane containing at least one silicon bonded hydrogen atom with the product of a lacunary polyoxometalate anion and a silane having two or three hydrolyzable groups.

The materials found in the prior art have uses in coatings; in electronics, for example as sensors; as magnetic/electric storage devices; as catalysts; as ion exchange membranes in chromatography and as self reinforced elastomers.

One objective of this invention is to prepare silane modified polyoxometalate anions using silanes having two hydrolyzable groups. Another objective of this invention is the preparation of materials which can potentially be used to catalyze stereospecific reactions or be used as building blocks for organic-silicone-inorganic polymers. These materials could also potentially be used as additives in polymers to perform specific functions, for example, electrical conductivity, photochromicity or electrochromicity.

SUMMARY OF THE INVENTION

The aforesaid objects of the present invention can be achieved by reacting a silane having two hydrolyzable groups with a polyoxometalate anion having a lacunary structure to form a silane modified polyoxometalate anion.

One embodiment of this invention provides silane modified polyoxometalate anions represented by the formula $$YZ(RR'Si)_n$$

where Z is selected from the group consisting of $M_{11}O_{39}^{-12}$, $M_9O_{34}^{-14}$ and $M_{17}O_{61}^{-20}$, where M is tungsten or molybdenum; Y is $As^{+5}$, $Si^{+4}$, $B^{+3}$, $Ge^{+4}$, $P^{+5}$ or $Fe^{+3}$ when Z is $M_{11}O_{39}^{-12}$, Y is $Si^{+4}$, $Ge^{+4}$, or $P^{+5}$ when Z is $M_9O_{34}^{-14}$, and Y is $As_2^{+10}$ or $P_2^{+10}$ when Z is $M_{17}O_{61}^{-20}$; R is a monovalent hydrocarbon radical having from 1 to 24 carbon atoms; R' is selected from the group consisting of a hydrogen atom and a monovalent hydrocarbon radical having from 1 to 24 carbon atoms and n represents the number of $(RR'Si)^{+2}$ groups bonding to the polyoxometalate anion and may have a value from 1 to 3.

The silane modified polyoxometalate products are anionic and therefore will associate with various cations. Some typical cations include hydrogen; alkali metals such as $Li^+$, $Na^+$, or $K^+$; alkaline earth metals such as $Ba^{+2}$, $Mg^{+2}$ or $Ca^{+2}$; or $R^2_4N^+$, where each $R^2$ represents a monovalent hydrocarbon radical that may or may not be identical to the other three $R^2$ radicals. The cation is preferably $R^2_4N^+$ where the $R^2$ radicals are preferably identical and are preferably alkyl containing from 1 to 10 or more carbon atoms such as methyl, ethyl, iso-propyl, butyl, hexyl or decyl and is most preferably butyl. The type of cation will influence the solubility characteristics of the products.

This invention also provides a method for preparing silane modified polyoxometalate anions, the method comprising reacting a silane having a general formula $$RR'SiX_2$$

where R is a monovalent hydrocarbon radical having from 1 to 24 carbon atoms, R' is selected from the group consisting of a hydrogen atom and a monovalent hydrocarbon radical having from 1 to 24 carbon atoms and X is a hydrolyzable group; with a polyoxometalate anion represented by the formula $$YZ$$

where Z is selected from the group consisting of $M_{11}O_{39}^{-12}$, $M_9O_{34}^{-14}$ and $M_{17}O_{61}^{-20}$, where M is tungsten or molybdenum; Y is $As^{+5}$, $Si^{+4}$, $B^{+3}$, $Ge^{+4}$, $P^{+5}$ or $Fe^{+3}$ when Z is $M_{11}O_{39}^{-12}$, Y is $Si^{+4}$, $Ge^{+4}$, or $P^{+5}$ when Z is $M_9O_{34}^{-14}$ and Y is $As_2^{+10}$ or $P_2^{+10}$ when Z is $M_{17}O_{61}^{-20}$.

DETAILED DESCRIPTION OF THE INVENTION

The Polyoxometalate Reactant

The polyoxometalate anion is represented by the formula YZ in the present invention. The letter Z describes various lacunary or deficient "isopolyanions," including $M_{11}O_{39}^{-12}$, $M_9O_{34}^{-14}$ and $M_{17}O_{61}^{-20}$, where M is a polyvalent metal. The letter Y describes various "heteroatoms" which together with the isopolyanion forms "heteropolyanions" of which polyoxometalate anions are a part.

In the present invention, M is preferably tungsten ($W^{+6}$) or molybdenum ($Mo^{+6}$) and most preferably tungsten. Y can be $As^{+5}$, $Si^{+4}$, $B^{+3}$, $Ge^{+4}$, $P^{+5}$ or $Fe^{+3}$ when Z is $M_{11}O_{39}^{-12}$, $Si^{+4}$, $Ge^{+4}$, or $P^{+5}$ when Z is $M_9O_{34}^{-14}$ and $As_2^{+10}$ or $P_2^{+10}$ when Z is $M_{17}O_{61}^{-20}$. When Z represents $M_{11}O_{39}^{-12}$ or $M_9O_{34}^{-14}$, in the present invention Y is preferably $Si^{+4}$ and $P^{+5}$ and most preferably $Si^{+4}$ and when Z is $M_{17}O_{61}^{-20}$ Y is preferably $P_2^{+10}$. Polyoxometalate anions have open valences and are therefore a charged species. The charge can be determined by multiplying the valences of the atoms associated with Y and Z by the value of the integer associated with that atom and adding the products together. For the polyoxometalate anion YZ where Y is $Si^{+4}$ and Z is $M_{11}O_{39}$ with M being tungsten or molybdenum, the charge is equal to the sum of the valence of silicon (+4), 11 times the valence of M (+6) and 39 times the valence of oxygen (–2), which totals –8.

Since the polyoxometalate anion has a negative charge, it will associate with various cations. Some typical cations are hydrogen; alkali metals such as $Li^+$, $Na^+$, or $K^+$; alkaline earth metals such as $Ba^{+2}$, $Mg^{+2}$ or $Ca^{+2}$; or $R^2_4N^+$, where each $R^2$ represents a monovalent hydrocarbon that may or may not be identical to the other three $R^2$ radicals The cation is preferably $R^2_4N^+$ where the $R^2$ radicals are preferably identical and are preferably alkyl containing from 1 to 10 or more carbon atoms such as methyl, ethyl, iso-propyl, butyl, hexyl and decyl and is most preferably butyl.

Methods for preparing lacunary polyoxometalate anions used as reactants for preparing the silane modified polyoxometalate anions of this invention are reported in the chemical literature, see for example, Inorganic Syntheses; Ginsberg, A. P., Ed., John Wiley & Sons, Vol. 27, Chapter 3, 1990. Specific references include Teze et al., J. Inorg. Nucl. Chem. (1977) 39, 999, for the preparation of the potassium salt of $SiW_{11}O_{39}^{8-}$, Herve et al., Inorg. Chem., (1977) 16, 2115 for the synthesis of the sodium salt of $SiW_9O_{34}^{10-}$ and Contant, R., Inorganic Syntheses; Ginsberg, A. P., Ed., John Wiley & Sons, Vol. 27, Chapter 3, pp 104–107, 1990, for the synthesis of the potassium salt of $(P_2W_{18}O_{62})^{6-}$. Non-lacunary or complete Keggin structures of polyoxometalate anions corresponding to the formula $YM_{12}O_{40}$ can be prepared by adding an acid to an aqueous solution of sodium tungstate or sodium molybdate in the presence of a solubilized compound, such as an alkali metal silicate, containing the heteroatom represented by Y in the general formula for the polyoxometalate anion. Another method for preparing non-lacunary polyoxometalate anions utilizes a phase transfer procedure described by Katsoulis and Pope, J. Am. Chem. Soc., (1984) 106, 2737. This procedure converts a water soluble polyoxometalate salt, such as an alkali metal polyoxometalate salt, to a salt that is soluble in non-polar organic solvents, such as a tetraalkylammonium polyoxometalate salt. In this instance the nitrogen bonded radicals should contain more than four carbon atoms and preferably six or seven carbon atoms.

In the present invention, lacunary polyoxometalate anions are reacted with silanes having two hydolyzable groups. The lacunary structures can be generated during preparation of the polyoxometalate anion by using the appropriate ratio of tungsten or molybdate salt to heteroatom compound corresponding to the formula of the desired structure and maintaining the pH of the reaction mixture at no lower than 4.8. Alternatively, a complete polyoxometalate anion structure can be changed to a lacunary structure by hydrolysis under basic conditions.

Specific reactants and conditions for preparing polyoxometalate anions are described in the literature so that a complete discussion of the subject is not required in this specification. The preparation of preferred polyoxometalate anions is described in the accompanying examples.

The Silane Reactant

The silane reactants used for modifying the polyoxometalate anions in the present invention are represented by the general formula $RR'SiX_2$. The letter X represents hydrolyzable groups bonded to silicon and R and R' represent other groups which may or may not be identical and which may or may not contain functionality also bonded to the silicon atom.

Hydrolyzable groups include any group attached to silicon which is hydrolyzed by water at room temperature. Suitable hydrolyzable groups that can be represented by X include but are not limited to halogen atoms such as chlorine, bromine, fluorine or iodine; groups of the formula —OT when T is any hydrocarbon or halogenated hydrocarbon group such as methyl, ethyl, iso-propyl, octadecyl, allyl, hexenyl, cyclohexyl, phenyl, benzyl, betaphenylether, 2-chloroethyl, chlorophenyl, 3,3,3-trifluoropropyl, or bromocyclohexyl; any hydrocarbon ether radical such as 2-methoxyethyl, 2-ethoxyisopropyl, 2-butoxyisobutyl, p-methoxyphenyl or —$(CH_2CH_2O)_2CH_3$; any acyl radical such as acetyl, propionyl, benzoyl, cyclohexoyl, acrylyl, methacrylyl, stearyl, naphthoyl, trifluoroacetyl, chlorobenzoyl or bromopropionyl; any acyloxy group such as acetoxy, benzoyloxy, propionoxy, or acryloxy; or any N,N-amino radical such as dimethylamino, diethylamino, ethylmethylamino, diphenylamino or dicyclohexylamino. X can also be any amino radical such as $NH_2$, dimethylamino, diethylamino, methylphenylamino or dicyclohexylamino; any ketoxime radical of the formula —ON=$CL_2$ or —ON=CL' in which L is any monovalent hydrocarbon or halogenated hydrocarbon as those shown for T above and L' is any divalent hydrocarbon radical both valences of which are attached to the carbon, such as hexylene, pentylene or octylene; ureido groups of the formula —N(L)CONL"$_2$ in which L is defined above and L" is H or any of the L radicals; carbamate groups of the formula —OOCNLL" in which L and L" are defined above; or carboxylic amide radicals of the formula —NLC=O(L") in which L and L" are defined above. X can also be the sulfate group or the sulfate ester groups of the formula —$OSO_2(OL)$ where L is as defined above; the cyano group; the isocyanate group; and the phosphate or phosphate ester groups of the formula —$OPO(OL)_2$ where L is as defined above. Halogen atoms, particularly chlorine, alkoxy groups containing from 1–4 carbon atoms, particularly methoxy and acyloxy groups containing 2–6 carbon atoms, particularly acetoxy are preferred based on cost and the nature of the byproducts generated during reaction with the polyoxometalalate anion.

Examples of suitable monovalent hydrocarbon radicals, including organofunctional radicals, that can be represented by R and R' include but are not limited to alkyl radicals such as methyl, ethyl, isopropyl, hexyl, octadecyl or myricyl; alkenyl radicals such as vinyl, allyl or hexenyl; alkynal radicals such as propargyl, cycloaliphatic radicals such as cyclopentyl, cyclohexyl or cyclohexenyl; aromatic hydrocarbons such as phenyl, tolyl, xylyl, xenyl, naphthyl or anthracyl; aralkyl hydrocarbon radicals such as benzyl, beta-phenylethyl, beta-phenylpropyl or gamma-tolylpropyl; halogenated hydrocarbon or carbon radicals such as 3,3,3-trifluoropropyl, tridecafluoro-1,1,2,2-tetrahydrooctyl)-1-methyl or perfluoroalkyl; epoxy radicals such as 2,3-epoxypropyl, epoxyethyl, 2-(3,4 epoxycyclohexyl) or 3,4 epoxybutyl; amino radicals such as aminoethyl, aminoethylaminopropyl, 2-aminobutyl, 3-aminopropyl or methyl aminopropyl; mercapto radicals such as 3-mercaptopropyl or mercaptomethyl; and methacrylo radicals such as 3-methacryloxypropyl In addition, R' may be represented by hydrogen. R and R' are preferably ethyl, methyl, vinyl, 1-hexenyl, phenyl, or 1,1,1,2,2,3,3,4,4-nonafluorohexyl, epoxy or amino. Most preferably one or both of the groups on R or R' is a functional group which is capable of further reaction such as vinyl, hexenyl, epoxy or amino.

If R and R' are not identical, the silicon atom is chiral and stereoisomers can form. This chirality creates the potential for designing stereospecific reactions using the present invention. These types of reactions are particularly utilized by the pharmaceutical industry in the production of drugs.

Methods for preparing silanes containing two hydrolyzable groups and various hydrocarbon groups or hydrogen are described in the art and so do not need to be described here. The preferred silanes used in the examples are all commercially available.

Reaction of the Polyoxometalate Anion with the Silane

Silane modified polyoxometalate anions having the general formula $YZ(RR^1Si)_n$ are prepared by reacting a silane containing two hydrolyzable groups with a lacunary polyoxometalate anion. The cation associated with the polyoxometalate anion is typically an alkali metal or tetralkyl ammonium.

The reaction between the polyoxometalate anion and the silane can be conducted in a homogeneous reaction or a heterogeneous reaction. The molar ratio of silane to polyoxometalate anion used in either type reaction can be from 0.5 mole to 3 moles silane per mole of polyoxometalate anion but should be greater than 1 and is preferably 2:1.

In a homogeneous reaction the silane and polyoxometalate anion are placed in a solvent in which both are soluble and allowed to stir for some time. If, for example, a chlorosilane is used in the presence of water, there is no need for the addition of another reagent because it will hydrolyze very quickly generating HCl which assists in the coordination of silane to polyoxometalate anion. When a silane other than a halosilane is used, for example an alkoxy silane, one will need to add a catalyst to assist in the hydrolysis/ coordination reaction. In most cases this is an acid or basic catalyst, preferably HCl. The amount of catalyst used can range from 0 to 2.5 equivalents per silane with 2 equivalents per silane being preferred. The reaction can take place at temperatures ranging from 0° C. to the boiling point of the solvent and are preferably conducted at ambient temperatures. Depending on temperature the time for reaction can range from minutes to hours and at ambient temperatures the reaction time is preferably 2–3 hours.

In a heterogeneous reaction, a polyoxometalate salt is brought into contact with a silane dissolved usually in an organic solvent such as acetonitrile or mixtures of acetonitrile/toluene and allowed to stir for several hours. As in the homogeneous reaction, it is preferred that the silane hydrolyses which is believed to assist in the coordination of silane to polyoxometalate anion. Therefore, when a silane other than a halosilane is used, for example an alkoxy silane, one will need to add a catalyst to assist in the hydrolysis/coordination reaction. In most cases this is an acid or basic catalyst, preferably HCl. The amount of catalyst used can range from 0 to 3 equivalents per silane with 2 equivalents per silane being preferred. A large excess of acid will convert the lacunary polyoxometalate anion to the "complete" Keggin structure thereby reducing the reaction yield. The reaction can take place at temperatures ranging from 0° C. to the boiling point of the solvent and is preferably conducted at ambient temperatures. Depending on temperature the time for reaction can range from 3 to 36 hours at ambient temperatures the reaction time is preferably 24 hours.

Whether the reaction is conducted in a heterogeneous manner or a homogeneous manner, the products can be isolated in similar ways. One method is simply by evaporating the solvent. This method can be used if the reaction is carried out using a polyoxometalate salt that is soluble in a nonpolar solvent such as toluene or methylene chloride. Another method to isolate the product is by adding a solvent that reduces the products' solubility, for example, from a water solution one could add ethanol, acetone or acetonitrile. If acetonitrile is the reaction solvent, one can add water and the product will precipitate.

The preferred method to isolate the products is to add another cation to the silane modified polyoxometalate product mixture which will then exchange with the cation that was initially added as the polyoxometalate salt to form another salt. This new salt will either precipitate out of the solvent used if it is insoluble in such solvent or can be precipitated out of solution by the addition of a different solvent. For example, if the solvent used is water, one can add organic cations such as tetrabutylammonium or inorganic cations such as $Ba^{+2}$, $Ca^{+2}$, $Cs^{+11}$ etc. and easily precipitate the product which is now associated with the new cation. If the solvent used is acetonitrile, one can add organic cations such as tetrabutylammonium bromide. In this case, the product associated with the new cation may not precipitate if it is soluble in acetonitrile, however, one can easily get this product to precipitate by the addition of water or other solvent which the product associated with the new cation does not have solubility.

In this invention it is preferable to prepare the silane modified polyoxometalate anion in acetonitrile by reacting an alkali metal salt of the polyoxometalate anion with a silane, adding tetrabutylammonium bromide to provide the tetrabutylammonium salt of the silane modified polyoxometalate anion and, if necessary, adding water to precipitate this salt out of solution. The silane modified polyoxometalate salts are stable in the absence of strong acids or bases in aqueous and nonaqueous environments.

Properties of Silane Modified Polyoxometalate Anions

Lacunary polyoxometalate anions such as $SiW_{11}O_{39}^{8-}$ have a vacancy or "hole" where a $WO^{4+}$ has been removed from a complete polyoxometalate anion such as $SiW_{12}O_{40}^{4-}$ and as illustrated in FIG. 1 four surface oxygen atoms are available for coordination. The chemical literature has shown that when this lacunary polyoxometalate anion is reacted with silanes containing three hydrolyzable groups, two silane groups bond to the four oxygens in the polyoxometalate anion and an oxygen bridge connects the two silane groups. The silane modified polyoxometalate anion resulting from the reaction of $SiW_{11}O_{39}^{8-}$ with $RR'SiX_2$ has a valence of 4-, ie. $SiW_{11}O_{39}O(RR'Si)_2^{4-}$. This valence is determined by adding the 2+ charge of each silane group to the charge of 8- of the lacunary polyoxometalate anion (2×(2+)+(8-)).

When a lacunary polyoxometalate anion is reacted with silanes containing two hydrolyzable groups an oxygen bridge connecting the two silane groups does not typically result. However, experiments have shown that if any of the R groups oxidize during the synthesis of the silane modified polyoxometalate anion an oxygen bridge can be observed in some of the reaction products as described in Examples 12, 13 and 14 herein.

It has also been determined that in some instances, reaction products may contain mixtures such that there are products containing two silane groups bonded to the polyoxometalate anion and products having only one silane group bonded to the polyoxometalate anion.

When only one silane group bonds to the lacunary polyoxometalate anion, two oxygen atoms remain with open valences and the resulting silane modified polyoxometalate anion has a valence which differs from the reaction product having two silane groups bonded to it. These two products are separable on the basis of overall negative charge. These results may be explainable as due to steric hindrance, ie. larger R or R' groups on silicon restrict how many groups can bond to the available oxygens.

In addition, it has been observed that increasing the molar concentration of the silane reactant may result in an increase in the monosubstituted reaction product.

If in the silane reactant $RR'SiX_2$, R and R' are not identical the silicon atoms are chiral and give rise to the formation of stereoisomers.

The physical properties of the silane modified polyoxometalate anions depend upon a number of variables including the cation associated with it. The cation will also determine the solvents that can be used as the reaction medium.

Silane modified polyoxometalate anions having functional groups bonded to the silicon atoms can serve as building blocks for the synthesis of silicone-polyoxometalate hybrid polymer systems with potential applications as coatings, as electronic or protonic conductors, as electronic and optical storage devices and as supported catalysts. If the silane modified polyoxometalate anions do not have functional groups bonded to the silicon, these materials still have various potential uses, for example, silane modified polyoxometalate anions containing R groups with long carbon chains may provide surfactant-like properties and therefore could be used to modify solvent properties.

EXAMPLES

The following examples describe preferred embodiments of the present silane modified polyoxometalate anions, the properties of these materials and methods for preparing them. The examples should not be interpreted as limiting the scope of the invention as defined in the claims.

Preparation of Salts of Preferred Polyoxometalate Anions

A. $K_8SiW_{11}O_{39}$

The salt of the polyoxometalate anion was prepared either according to the method described by Teze et al., J. Inorg. Nucl. Chem (1977) 39, 999 or with simple modifications thereto. Into a flask equipped with a stirrer, addition funnel and Claisen "Y" adapter fitted with a condenser and thermometer was charged 900 mL deionized water, 546 g (1.66 moles) of sodium tungstate, $Na_2WO_4 \cdot 2H_2O$ and 33 g (0.155 moles) of sodium metasilicate, $Na_2SiO_3 \cdot 5H_2O$. The mixture was heated at 95° C. until the solids dissolved and then 585 mL (2.34 moles) 4N aqueous hydrochloric acid was added over about 3 hours. The heating was continued for another 15 minutes after all the HCl was added and then the solution was filtered hot through a set of #5 and #3 Whatman filters in a nitrogen pressurized filter funnel. A first white precipitate weighing 0.059 g was collected. The clear first filtrate was transferred to a beaker, kept hot at 80° C. and 225 g (2.98 moles) potassium chloride, KCl was added. The solution was stirred for another 20 minutes during which time a second white precipitate formed. This second precipitate was filtered as described above, washed three times with 100 mL cold deionized water and dried for 24 hours at 110° C. to a powder giving a 65% yield of $K_8SiW_{11}O_{39}$ based on $Na_2WO_4*H_2O$. As the second filtrate cooled, more of the second precipitate appeared. This additional second precipitate was gravity filtered through a #1 Whatman paper, transferred to a fritted glass Buchner funnel fitted with a 1.2 um membrane filter, washed well with cold deionized water and dried to a constant weight first for 24 hours at 115° C. and then for 28 hours at 125° C. giving a final yield of $K_8SiW_{11}O_{39}$ of 42.5 g or 81% based on $Na_2WO_4*H_2O$. The product was identified by its infrared spectra and by the use of $^{29}Si$ nuclear magnetic resonance spectroscopy (NMR) and $^{183}W$ NMR.

B. $Na_7PW_{11}O_{39}*nH_2O$

This salt was prepared according to the method of Brevard et al., J. A. Chem. Soc. (1983), 105, 7059. An amount of 72.5 g (0.22 moles) $Na_2WO_4*2H_2O$ and 2.87 anhydrous $Na_2HPO_3$ (0.02 moles) were dissolved in approximately 200 mL of deionized water. The solution was heated to 80°–90° C. and titrated to pH 4.8 using 21.8 mL concentrated $HNO_3$. The volume of the solution was reduced to half and the polyoxometalate salt separated in a dense lower layer by liquid-liquid extraction with 90 mL of acetone. The extraction was repeated two more times and only a small amount of lower layer was separated. The solid sodium salt was obtained as the hydrate by evaporating the acetone extract to dryness (approximately 10 days in air.) The material was characterized by IR and NMR spectroscopy.

Preparation of the Tetrabutylammonium Salt of Silane Modified Polyoxometalate Anions Unless otherwise specified, the reactions were conducted at ambient temperature and all yield percentages in the examples are by weight. The method to prepare silane modified polyoxometalate anions described by Judenstein, Chem. Mater. (1992) 4,4, has been used in the present invention, with some modifications.

EXAMPLE 1

In a flask equipped with a magnetic stirrer and containing 450 mL acetonitrile, $CH_3CN$, 15 g ($5 \times 10^{-3}$ moles) $K_8SiW_{11}O_{39}$ dried overnight at 115°–117° C. was added and allowed to stir for 2 hours. To that mixture 0.73 g ($9.2 \times 10^{-3}$ moles) pyridine, $C_5H_5N$ was added. An amount of 1.20 g ($9.3 \times 10^{-3}$ moles) dimethyldichlorosilane, $(CH_3)_2SiCl_2$ dissolved in 17 g $CH_3CN$ was then added over a 16 minute period. An additional 6.7 mL $CH_3CN$ used to rinse the addition funnel was added to the flask and the mixture stirred another 22 hours. A first precipitate consisting of unreacted $K_8SiW_{11}O_{39}$ and potassium chloride was separated by centrifuging and filtering through a 0.22 um nylon membrane filter. To the clear first filtrate, 48.55 g (0.15 moles) tetrabutylammonium bromide $(C_4H_9)_4NBr$ was added and the mixture stirred for 15 minutes. A second precipitate formed and was separated as before. To the second filtrate, 450 mL deionized water was added and a third precipitate formed. This third precipitate was isolated by centrifuging and decanting the liquid part, washing the precipitate twice with 100 mL portions of deionized water and air drying. Analysis by $^{29}Si$ NMR and $^{183}W$ NMR showed the third precipitate consisted of the mixed adduct $[(C_4H_9)_4N]_{(8-2n)}SiW_{11}O_{39}[(CH_3)_2Si]_n$ where n=1 and 2. The mole ratio of $K_8SiW_{11}O_{39}/(CH_3)_2SiCl_2$ added initially was 1/1.84 and the mole ratio of isolated adduct n=1/n=2, estimated from $^{29}Si$ NMR data was 1.6/1. Yield of the product was 7.99 g. This yield was estimated as 40% based on $K_8SiW_{11}O_{39}$ and the adduct ratio.

EXAMPLE 2

In a flask equipped with a stirrer and containing 450 mL acetonitrile, $CH_3CN$, 15 g ($5 \times 10^{-3}$ moles) $K_8SiW_{11}O_{39}$ dried overnight at 115°–117° C. was added and allowed to stir for 2 hours. An amount of 0.774 g ($6 \times 10^{-3}$ moles) $(CH_3)_2SiCl_2$ dissolved in 10 g $CH_3CN$, was added to the flask and the mixture stirred another 40 hours. A first precipitate consisting of unreacted $K_8SiW_{11}O_{39}$ and potassium chloride was separated by centrifuging and filtering through a 0.22 um nylon membrane filter. To the first clear filtrate, 48.35 g (0.15 moles) tetrabutylammonium bromide, $(C_4H_9)_4NBr$ was added and the mixture stirred for 15 minutes. A second precipitate formed and was separated as before. To the second filtrate, 400 mL deionized water was added and a third white precipitate formed. This third precipitate was recovered by centrifuging, decanting, filtering, washing several times with deionized water and drying under a nitrogen purge for 72 hours. Analysis by $^{29}Si$ NMR and $^{183}W$ NMR showed the third precipitate consisted of the mixed adduct $[(C_4H_9)_4N]_{(8-2n)}SiW_{11}O_{39}[(CH_3)_2Si]_n$ where n=1 and 2. The mole ratio of $K_8SiW_{11}O_{39}/(CH_3)_2SiCl_2$ added initially was 1/1.20 and the mole ratio of isolated adduct n=1/n=2, estimated from $^{29}Si$ NMR data was 2.3/1. Yield of the product was 10.17 g. This yield was estimated as 54% based on $K_8SiW_{11}O_{39}$ and the adduct ratio.

EXAMPLE 3

This preparation followed the same general procedure as in Example 2 except the amount of $(CH_3)_2SiCl_2$ added was 1.2 g ($9.3 \times 10^{-3}$ moles). Analysis by $^{29}Si$ NMR and $^{183}W$ NMR showed the third precipitate consisted of the mixed adduct $[(C_4H_9)_4N]_{8-2n}SiW_{11}O_{39}[(CH_3)_2Si]_n$ where n=1 and 2. The mole ratio of $K_8SiW_{11}O_{39}/(CH_3)_2SiCl_2$ added initially was 1/1.86 and the mole ratio of isolated adduct n=1/n=2, estimated from $^{29}Si$ NMR data was 3.8/1. Yield of the product was 14.95 g. This yield was estimated as 73% based on $K_8SiW_{11}O_{39}$ and the adduct ratio.

EXAMPLE 4

This preparation followed the same general procedure as in Example 2 except the amount of $(CH_3)_2SiCl_2$ added was 1.55 g ($1.2 \times 10^{-2}$ moles). Analysis by $^{29}Si$ NMR and $^{183}W$ NMR showed the third precipitate consisted of the mixed adduct $[(C_4H_9)_4N]_{(8-2n)}SiW_{11}O_{39}[(CH_3)_2Si]_n$ where n=1 and 2. The mole ratio of $K_8SiW_{11}O_{39}/(CH_3)_2SiCl_2$ added initially was 1/2.4 and the mole ratio of isolated adduct n=1/n=2, estimated from $^{29}Si$ NMR data was 17.8/1. Yield of the product was 15.32 g. This yield was estimated as 74% based on $K_8SiW_{11}O_{39}$ and the adduct ratio.

EXAMPLE 5

In a flask equipped with a stirrer and containing 450 mL acetonitrile, $CH_3CN$, 15 g ($5 \times 10^{-3}$ moles) $K_8SiW_{11}O_{39}$ dried overnight at 115° C. was added and allowed to stir for 2 hours. An amount of 1.91 g (0.01 moles) $(CH_3)C_6H_5SiCl_2$ dissolved in 1.5 g $CH_3CN$, was added dropwise over one minute and the mixture stirred 22 hours. A first precipitate was separated by centrifuging and filtering through a 0.22 um nylon membrane filter. To the first clear filtrate, 48.65 g (0.15 moles) tetrabutylammonium bromide, $(C_4H_9)_4NBr$ was added and the mixture stirred for 15 minutes. A second precipitate formed and was separated as before. To the second filtrate, 500 mL deionized water was added and a third precipitate formed. This third precipitate was recovered by centrifuging, decanting, filtering, washing several times with deionized water and drying under a nitrogen purge. Analysis by $^{29}Si$ NMR and $^{183}W$ NMR showed the third precipitate consisted of the mixed adduct $[(C_4H_9)_4N]_{8-2n}Si*W_{11}O_{39}[(CH_3)C_6H_5Si]_n$, where n=1 and 2 and the Si* being a chiral center. Two monosubstituted stereoisomers exemplified by structures (a) and (b), following Example 14, were present and a disubstituted isomer as exemplified by structure (c), presumably where R=methyl, was also found. The mole ratio of $K_8SiW_{11}O_{39}/(CH_3)C_6H_5SiCl_2$ added initially was 1/2. Yield of the product was 17.51 g. This yield was estimated as 82% based on $K_8SiW_{11}O_{39}$.

EXAMPLE 6

In a flask equipped with a stirrer and containing 450 mL $CH_3CN$, 18.08 g ($8.1 \times 10^{-3}$ moles) $K_8SiW_{11}O_{39}$ dried for 24 hours at 115° C. was added and the milky suspension stirred for 2 hours. An amount of 1.72 g (0.0122 moles) methylvinyldichlorosilane $ViCH_3SiCl_2$ was added and allowed to stir for 23 hours. The mixture was centrifuged, a first precipitate isolated and the clear supernatant solution decanted to a clean flask. An amount of 58.22 g (0.181 moles) tetrabutylammonium bromide was added to this first filtrate and the mixture stirred for 15 minutes. A second fluffy white precipitate formed and was isolated by filtering through a 0.22 um nylon membrane. To the remaining clear, slightly yellow filtrate, 600 mL deionized water was added and a third precipitate formed. This third precipitate was isolated by centrifuging and decanting the liquid part, washing the precipitate with deionized water and drying under nitrogen. Analysis by $^{29}Si$ NMR and $^{183}W$ NMR showed the third precipitate consisted of two isomers of the adduct $[(C_4H_9)_4N]_6SiW_{11}O_{39}[CH_3Si*Vi]$, the Si* being a chiral center. These isomers are exemplified by structures (a) and (b), following Example 14, where R=methyl and R'=vinyl. The $^{183}W$ NMR spectrum was more helpful than the $^{29}Si$ NMR spectrum for determining the relative amounts of each isomer. A 22 line spectrum was obtained which corresponded to two sets of 11 equivalent lines. Based on the equivalent amounts of the two isomers present in the mixture, it was concluded that the preference was statistical. The mole ratio of $K_8SiW_{11}O_{39}/(CH_3)ViSiCl_2$ added initially was 1/1.5. Yield of the reaction product was 10.98 g. This yield was estimated as 43.2% based on $K_8SiW_{11}O_{39}$.

EXAMPLE 7

In a flask equipped with a stirrer and containing 450 mL acetonitrile, $CH_3CN$, 15 g ($5 \times 10^{-3}$ moles) $K_8SiW_{11}O_{39}$ dried overnight at 115° C. was added and allowed to stir for 2 hours. An amount of 1.88 g (0.01 moles) $(CH_3)ViSi(O_2CCH_3)_2$ was added and the mixture stirred 24 hours. A considerable amount of $K_8SiW_{11}O_{39}$ remained undissolved and so 2.02 g (0.02 moles) concentrated HCl was added dropwise into the mixture over a period of 4 minutes and the stirring continued for another 20 hours. A first precipitate was separated by centrifuging and filtering through a 0.22 um nylon membrane filter. To the first clear filtrate, 48.65 g (0.15 moles) tetrabutylammonium bromide, $(C_4H_9)_4NBr$ was added and the mixture stirred for 15 minutes. A second precipitate formed and was separated as before and the weight of the dry powder was 6.05 g. To the second filtrate, 500 mL deionized water was added and a third precipitate formed. This third precipitate was recovered by centrifuging, decanting, filtering, washing several times with deionized water and drying under a nitrogen purge. Final weight of third precipitate was 12.86 g. Analysis by IR indicated that the second and third precipitates were identical. Analysis by $^{29}Si$ NMR and $^{183}W$ NMR showed the second and third precipitates consisted of two isomers of the adduct $[(C_4H_9)_4N]_6SiW_{11}O_{39}[CH_3Si*Vi]$, the Si* being a chiral center, the same compounds as described in Example 6. These isomers are exemplified by structures (a) and (b), following Example 14, where R=methyl and R'=vinyl. The mole ratio of $K_8SiW_{11}O_{39}/(CH_3)ViSi(O_2CCH_3)_2$ added initially was 1/2. Yield of the product based on the second and third precipitates was 12.86 g. This yield was estimated as 92% based on $K_8SiW_{11}O_{39}$.

EXAMPLE 8

In a flask equipped with a stirrer and containing 450 mL acetonitrile, $CH_3CN$, 15 g ($5 \times 10^{-3}$ moles) $K_8SiW_{11}O_{39}$ dried overnight at 115° C. was added and allowed to stir for 2 hours. An amount of 2.48 g (0.01 moles)

dissolved in 3.98 g $CH_3CN$ was added to the mixture. An amount of 1.97 g (0.02 moles) concentrated HCl was added dropwise into the mixture and the stirring continued for another 22 hours. A first precipitate was separated by centrifuging and decanting. To the first clear filtrate, 48.65 g (0.15 moles) tetrabutylammonium bromide, $(C_4H_9)_4NBr$ was added and the mixture stirred for 15 minutes. A second precipitate formed and was separated by filtering through a 0.22 um nylon membrane. To the second filtrate, 800 mL deionized water was added and a third precipitate formed. This third precipitate was recovered by centrifuging, decanting, filtering, washing several times with deionized water and drying under a nitrogen purge. Analysis by $^{29}Si$ NMR and $^{183}W$ NMR showed the third precipitate consisted of two isomers of the adduct

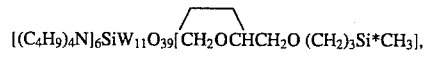

the Si* being a chiral center, as exemplified by structures (a) and (b), following Example 14. Both the $^{183}W$ NMR and the $^{29}Si$ NMR data were very similar to that received in analyzing the hexenyl silane modified polyoxometalate described in Example 9. The mole ratio of

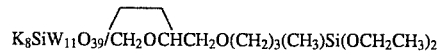

added initially was 1/2. Yield of the product based on the third precipitate was 16.18 g. This yield was estimated as 75% based on $K_8SiW_{11}O_{39}$.

EXAMPLE 9

In a flask equipped with a stirrer and containing 450 mL $CH_3CN$, 15.0 g ($5.0\times10^{-3}$ moles) $K_8SiW_{11}O_{39}$ dried for 24 hours at 115° C. was added and the milky suspension stirred for 2 hours. An amount of 1.98 g (0.01 moles) 1-hexenyl-methyldichlorosilane $CH_2=CH(CH_2)_4(CH_3)SiCl_2$ was added and the solution stirred for an additional 21 hours. The mixture was centrifuged and a clear supernatant solution was separated from a first precipitate by decanting it to a clean flask. An amount of 48.35 g (0.146 moles) tetrabutylammonium bromide was added to the supernatant solution and the mixture stirred for 15 minutes. A second fluffy white precipitate formed and was isolated by filtering through a 0.22 um nylon membrane. To the remaining clear, slightly yellow filtrate, 500 mL deionized water was added and a third precipitate formed. This third precipitate was isolated by centrifuging and decanting the liquid part, washing the precipitate three times with about 170 mL of deionized water and drying under nitrogen. Analysis by $^{29}Si$ NMR and $^{183}W$ NMR showed the third precipitate consisted of two isomers of the adduct $[(C_4H_9)_4N]_6SiW_{11}O_{39}[CH_3Si*(CH_2)_4CH=CH_2]$, the Si* being a chiral center, as exemplified by structures (a) and (b), following Example 14. The $^{183}W$ NMR spectrum was more helpful than the $^{29}Si$ NMR spectrum for determining the relative amounts of each isomer. A 22 line spectrum was obtained with relative intensities of about 1:0.6. This suggests that the composition of the mixture is approximately 63:37, however we were not able to determine which isomer corresponded to which set of resonances. The mole ratio of $K_8SiW_{11}O_{39}/CH_2=CH(CH_2)_4(CH_3)SiCl_2$ added initially was 1/2. Yield of the reaction product was 16.34 g. This yield was estimated as 76.5% based on $K_8SiW_{11}O_{39}$.

EXAMPLE 10

In a flask equipped with a stirrer and containing 450 mL $CH_3CN$, 15.0 g ($5.0\times10^{-3}$ moles) $Na_7PW_{11}O_{39}$ dried for 24 hours at 115° C. and ground in a mortar and pestle was added and the milky suspension stirred for 2.5 hours. An amount of 2.08 g (0.01 moles) 1-hexenylmethyldichlorosilane $CH_2=CH(CH_2)_4(CH_3)SiCl_2$ dissolved in $CH_3CN$ was added and the solution stirred for an additional 22 hours. The mixture was centrifuged and a slightly yellow supernatant solution was separated from a first precipitate by decanting it to a clean flask. An amount of 51.26 g (0.146 moles) tetrabutylammonium bromide was added to the supernatant solution and the mixture stirred for 15 minutes. A second precipitate formed and was isolated by filtering through a 0.22 um nylon membrane. To the remaining clear, slightly yellow filtrate, 500 mL deionized water was added and a third precipitate formed. This third precipitate was isolated by centrifuging and decanting the liquid part, washing the precipitate three times with about 170 mL of deionized water and drying under nitrogen. Analysis by $^{31}P$ NMR, $^{29}Si$ NMR and $^{183}W$ NMR showed the third precipitate consisted of two monosubstituted isomers of the type described in Example 9 above. The mole ratio of $Na_7PW_{11}O_{39}/CH_2=CH(CH_2)_4(CH_3)SiCl_2$ added initially was 1/2. Yield of the product was 15.88 g. This yield was estimated as 75% based on $Na_7PW_{11}O_{39}$.

EXAMPLE 11

In a flask equipped with a stirrer and containing 450 mL $CH_3CN$, 15.0 g ($5.0\times10^{-3}$ moles) $K_8SiW_{11}O_{39}$ dried for 24 hours at 115° C. was added and the milky suspension stirred for 2 hours. An amount of 3.58 g (0.01 moles) $CF_3(CF_2)_3CH_2CH_2(CH_3)SiCl_2$ dissolved in 1.97 g $CH_3CN$ was added and the solution stirred for an additional 24 hours. The mixture was centrifuged and the supernatant solution was separated from a first precipitate by decanting it to a clean flask. An amount of 48.35 g (0.15 moles) tetrabutylammonium bromide was added to the supernatant solution and the mixture stirred for 15 minutes. A second precipitate formed and was isolated by filtering through a 0.22 um nylon membrane. To the remaining clear, slightly yellow filtrate, 500 mL deionized water was added causing the product to precipitate slowly. This third precipitate was isolated by centrifuging and decanting the liquid part, washing the precipitate three times with about 540 mL of deionized water and drying under nitrogen. Analysis by $^{29}Si$ NMR and $^{183}W$ NMR showed the third precipitate consisted of the mixed adduct $[(C_4H_9)_4N]_{8-2n}SiW_{11}O_{39}[CF_3(CF_2)_3CH_2CH_2(CH_3)Si*]_n$ where n=1 and 2 and the Si* being a chiral center. Two monosubstituted stereoisomers exemplified by the structures (a) and (b), following Example 14, were present and two disubstituted isomers as exemplified by structures (d) and (e), following Example 14, presumably where $R=CF_3(CF_2)_3CH_2CH_2-$, were also found. The mole ratio of $K_8SiW_{11}O_{39}/CF_3(CF_2)_3CH_2CH_2(CH_3)SiCl_2$ added initially. Yield of the product was 18.76 g. This yield was estimated as 86.5% based on $K_8SiW_{11}O_{39}$ and adduct ratio. The product was very soluble in $CH_3CN$ (60 weight percent), DMSO and $(CH_3)_2CO$.

EXAMPLE 12

In a flask equipped with a stirrer and containing 450 mL acetonitrile, $CH_3CN$, 15 g ($5\times10^{-3}$ moles) $K_8SiW_{11}O_{39}$ dried overnight at 115°–117° C. was added and allowed to stir for 2 hours. An amount of 1.15 g (0.01 moles) methylhydrogendichlorosilane, $HCH_3SiCl_2$ dissolved in 17 g $CH_3CN$ was then added over an 8 minute period. An additional 6 mL of $CH_3CN$ used to rinse the addition funnel was added to the flask and the mixture stirred another 21 hours. A first precipitate consisting of unreacted $K_8SiW_{11}O_{39}$ and potassium chloride was separated by centrifuging and filtering through a 0.22 um nylon membrane filter. To the clear first filtrate, 48.35 g (0.15 moles) tetrabutylammonium bromide $(C_4H_9)_4NBr$ was added and the mixture stirred for 27 minutes. A second precipitate formed and was separated as before. To this second filtrate, 450 mL deionized water was added and a third precipitate formed. This third precipitate was isolated by centrifuging and decanting the liquid part, washing the precipitate twice with 100 mL portions of deionized water and drying under nitrogen. Analysis by $^{29}Si$ NMR and $^{183}W$ NMR showed the third precipitate consisted of three isomers of the adduct $[(C_4H_9)_4N]_4Si*W_{11}O_{39}[CH_3SiH]_2$, the Si* being a chiral center, as exemplified by structures (c), (d) and (e), following Example 14. In addition, it appears that a large portion of the Si—H of the silane starting material oxidized during the synthesis of the silane modified polyoxometalate and produced a material having the formula $SiW_{11}O_{39}O[SiCH_3]_2^{-4}$ as exemplified by structure (f), following Example 14. Approximately 50% of the product was the oxidized material exemplified by structure (f), isomers exemplified by structures (c) and (d) comprised most of the remaining 50% and the isomer exemplified by structure (e) seemed to make up only a very small percentage. The mole ratio of $K_8SiW_{11}O_{39}/(CH_3)HSiCl_2$ added initially was 1/2. Yield of the product was 2.85 g. This yield was estimated as 15% based on $K_8SiW_{11}O_{39}$.

EXAMPLE 13

In a flask equipped with a stirrer and containing 450 mL $CH_3CN$, 15.0 g ($5.0\times10^{-3}$ moles) $Na_7PW_{11}O_{39}$ dried for 24 hours at 115° C. and ground in a mortar and pestle was added and the milky suspension stirred for 2 hours. An amount of 1.22 g (0.01 moles) $H(CH_3)SiCl_2$ dissolved in $CH_3CN$ was added and the solution stirred for an additional 20 hours. The mixture was centrifuged and a slightly yellow supernatant solution was separated from a first precipitate by decanting it to a clean flask. An amount of 51.26 g (0.146 moles) tetrabutylammonium bromide was added to the supernatant solution and the mixture stirred for 15 minutes. A second precipitate formed and was isolated by filtering through a 0.22 um nylon membrane. To the remaining clear, yellow filtrate, 500 mL deionized water was added and a third precipitate formed. This third precipitate was isolated by centrifuging and decanting the liquid part, washing the precipitate with deionized water and drying under nitrogen. Analysis by $^{29}Si$ NMR and $^{183}W$ NMR showed the third precipitate consisted entirely of the oxidized product exemplified by structure (f), following Example 14. The mole ratio of $Na_7PW_{11}O_{39}/H(CH_3)SiCl_2$ added initially was 1/2. Yield of the product was 15.14 g. This yield was estimated as 80.9% based on $Na_7PW_{11}O_{39}$.

EXAMPLE 14

In a flask equipped with a stirrer and containing 450 mL acetonitrile, $CH_3CN$, 14.65 g ($5\times10^{-3}$ moles) $K_8SiW_{11}O_{39}$ dried overnight at 115°–117° C. was added and allowed to stir for 2 hours. An amount of 1.26 g (0.01 moles) ethylhydrogendichlorosilane, $H(CH_3CH_2)SiCl_2$ dissolved in 1 g $CH_3CN$ was then added and the stirring continued for 23.5 hours. After centrifugation, a first precipitate was separated from the supernatant liquid by decanting. To the clear first filtrate, 48.65 g (0.146 moles) tetrabutylammonium bromide $(C_4H_9)_4NBr$ was added and a second precipitate formed and was separated by filtering through a 0.22 um nylon membrane and washing with approximately 10–15 mL $CH_3CN$. This second precipitate was dried under nitrogen and the yield was 17.79 g. To the second filtrate, 500 mL deionized water was added and a very small amount of third precipitate formed. This third precipitate was isolated by centrifuging and decanting the liquid part, washing with deionized water and drying under nitrogen. The weight of the dried third precipitate was 0.79 g. IR analysis indicated that the second and third precipitates were identical. Analysis by $^{29}Si$ NMR and $^{183}W$ NMR of the second precipitate showed that it consisted of two isomers of the adduct $[(C_4H_9)_4N]_4Si^*W_{11}O_{39}[CH_3CH_2SiH]_2$, the Si* being a chiral center, as exemplified by the structures (d) and (e) following this example. In addition, it appears that approximately 30% of the Si—H of the silane starting material oxidized during the synthesis of the silane modified polyoxometalate and produced a material having the formula $SiW_{11}O_{39}O[SiCH_2CH_3]_2^{-4}$ as exemplified by structure (f) following this Example. Based on the equivalent amounts of the two isomers present in the mixture, it was concluded that the preference was statistical. The mole ratio of $K_8SiW_{11}O_{39}/(CH_3CH_2)HSiCl_2$ added initially was 1/2. Yield of the product was 17.79 g. This yield was estimated as 96.26% based on $K_8SiW_{11}O_{39}$ and assuming 100% pure adduct. Structures (a) through (f) are schematic representations showing the coordination of silanes and surface oxygens (small circles) on the polyoxometalate anion (large circles) to form silane modified polyoxometalate adducts.

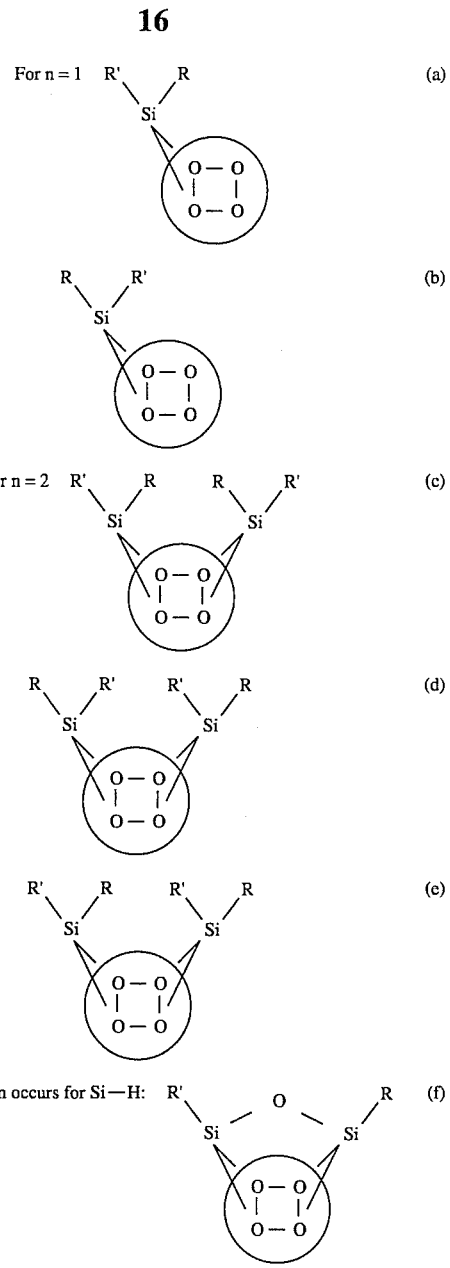

We claim:

1. A silane modified polyoxometalate anion represented by the formula $$YZ(SiRR')_n$$

where Z is selected from the group consisting of $M_{11}O_{39}^{-12}$, $M_9O_{34}^{-14}$ and $M_{17}O_{61}^{-20}$, where M is tungsten or molybdenum; Y is $As^{+5}$, $Si^{+4}$, $B^{+3}$, $Ge^{+4}$, $P^{+5}$ or $Fe^{+3}$ when Z is $M_{11}O_{39}^{-12}$, Y is $Si^{+4}$, $Ge^{+4}$, or $P^{+5}$ when Z is $M_9O_{34}^{-14}$ and Y is $As_2^{+10}$ when $P_2^{+10}$ when Z is $M_{17}O_{61}^{-20}$; R is selected from the group consisting of monovalent hydrocarbon radicals having from 1 to 24 carbon atoms, monovalent halogenated hydrocarbon or carbon radicals having from 1 to 24 carbon atoms and monovalent hydrocarbon radicals having from 1 to 24 carbon atoms substituted with an epoxy group, an amino group, a mercapto group or a methacrylo group; R' is selected from the group consisting of a hydrogen atom and R; and n represents the number of (=SiRR')$^{+2}$ groups bonding to the polyoxometalate anion and has a value from 1 to 3.

2. The anion according to claim 1 and further comprising an associated cation selected from the group consisting of an alkali metal and tetralkylammonium.

3. The anion according to claim 1 wherein R and R' are not identical.

4. The anion according to claim 1, wherein Z is $M_{11}O_{39}^{-12}$ where M is tungsten, Y is $Si^{+4}$ and n has a value from 1 to 2.

5. The anion according to claim 2, wherein Z is $M_{11}O_{39}^{-12}$ where M is tungsten, Y is $Si^{+4}$ and n has a value from 1 to 2.

6. The anion according to claim 2, wherein R is selected from the group consisting of monovalent hydrocarbon radicals having from 1 to 10 carbon atoms, monovalent halogenated hydrocarbon or carbon radicals having from 1 to 10 carbon atoms and monovalent hydrocarbon radicals having from 1 to 10 carbon atoms substituted with an epoxy group, an amino group, a mercapto group or a methacrylo group.

7. The anion according to claim 2, wherein R' is selected from the group consisting of monovalent hydrocarbon radicals having from 1 to 10 carbon atoms, monovalent halogenated hydrocarbon or carbon radicals having from 1 to 10 carbon atoms and monovalent hydrocarbon radicals having from 1 to 10 carbon atoms substituted with an epoxy group, an amino group, a mercapto group or a methacrylo group.

8. The anion according to claim 5, wherein R is selected from the group consisting of monovalent hydrocarbon radicals having from 1 to 10 carbon atoms, monovalent halogenated hydrocarbon or carbon radicals having from 1 to 10 carbon atoms and monovalent hydrocarbon radicals having from 1 to 10 carbon atoms substituted with an epoxy group, an amino group, a mercapto group or a methacrylo group.

9. The anion according to claim 5, wherein R' is selected from the group consisting of monovalent hydrocarbon radicals having from 1 to 10 carbon atoms, monovalent halogenated hydrocarbon or carbon radicals having from 1 to 10 carbon atoms and monovalent hydrocarbon radicals having from 1 to 10 carbon atoms substituted with an epoxy group, an amino group, a mercapto group or a methacrylo group.

10. The anion according to claim 9 wherein R is selected from the group consisting of vinyl, 1-hexenyl and monovalent hydrocarbon radicals having from 1 to 10 carbon atoms substituted with an epoxy group or an amino group.

* * * * *